(12) United States Patent
Ibrahimovic et al.

(10) Patent No.: US 11,958,714 B2
(45) Date of Patent: Apr. 16, 2024

(54) EQUIPMENT FOR WINDING MEDICAL TUBING

(71) Applicant: Mikron Switzerland AG, Succursale Boudry, Automation, Boudry (CH)

(72) Inventors: Hazret Ibrahimovic, Marin-Epagnier (CH); Philippe Jacquot, Pontarlier (CH); Roger Ritter, Bienne (CH)

(73) Assignee: Mikron Switzerland SA, Succursale Boudry, Automation, Boudry (CH)

( * ) Notice: Subject to any disclaimer, the term of this patent is extended or adjusted under 35 U.S.C. 154(b) by 329 days.

(21) Appl. No.: 17/603,900

(22) PCT Filed: Apr. 14, 2020

(86) PCT No.: PCT/IB2020/053491
§ 371 (c)(1),
(2) Date: Oct. 14, 2021

(87) PCT Pub. No.: WO2020/212834
PCT Pub. Date: Oct. 22, 2020

(65) Prior Publication Data
US 2022/0219936 A1     Jul. 14, 2022

(30) Foreign Application Priority Data

Apr. 15, 2019  (EP) .................................. 19169329
Jun. 7, 2019   (EP) .................................. 19179055

(51) Int. Cl.
*B65H 54/58*     (2006.01)
*A61M 39/08*     (2006.01)
(Continued)

(52) U.S. Cl.
CPC ............. *B65H 54/58* (2013.01); *A61M 39/08* (2013.01); *B65B 7/00* (2013.01); *B65B 35/16* (2013.01);
(Continued)

(58) Field of Classification Search
None
See application file for complete search history.

(56) References Cited

U.S. PATENT DOCUMENTS 2,896,386 A * 7/1959 Marsh ..................... B65B 63/06
                                                28/291
4,162,600 A * 7/1979 Westall ................... B65B 13/02
                                                53/590

(Continued)

FOREIGN PATENT DOCUMENTS

CN      103523560 A     1/2014
CN      108313424 A     7/2018
(Continued)

OTHER PUBLICATIONS

"Welcome to Medical Systems for Industry", Medical Systems for Industry, info@medicalsysforindustry.com; 2021; 1 pg.
(Continued)

*Primary Examiner* — Tanzim Imam
(74) *Attorney, Agent, or Firm* — Blank Rome LLP

(57) ABSTRACT

The present invention discloses an equipment for winding medical tubing, employing automated, sequentially-arranged workstations (1, 5, 7) capable of operating simultaneously, comprising one or more conveying units (2), one or more bending units (3) for arranging medical tubing (10) in a U shape, one or more loading units (4), one or more winding stations (5) for winding medical tubing (10), one or more unloading units (6) and, optionally, one or more packaging units (7).

15 Claims, 7 Drawing Sheets

(51) Int. Cl.
- *B65B 7/00* (2006.01)
- *B65B 35/16* (2006.01)
- *B65B 63/04* (2006.01)
- *B65H 54/62* (2006.01)

(52) U.S. Cl.
CPC ....... *B65B 63/04* (2013.01); *A61M 2039/087* (2013.01); *B65H 2701/33* (2013.01)

(56) References Cited

U.S. PATENT DOCUMENTS

| | | | | |
|---|---|---|---|---|
| 4,253,289 | A | * | 3/1981 | Cole ............ B65H 54/62 53/73 |
| 6,135,164 | A | * | 10/2000 | Celoudoux ............ H01R 43/28 140/102 |
| 2013/0006226 | A1 | | 1/2013 | Hong et al. |
| 2018/0008798 | A1 | | 1/2018 | Quiroz et al. |

FOREIGN PATENT DOCUMENTS

| | | |
|---|---|---|
| DE | 3523848 A1 | 1/1987 |
| EP | 1452474 A1 | 9/2004 |

OTHER PUBLICATIONS

"Catheter Manufacturing, Testing and Packaging Equipment for Catheter Production; also packaging materials for catheters", Medical Systems for Industry, info@medicalsysforindustry.com; 2021; 1 pg.

"Tubing Coiling Equipment—Medical Tubing Processing Machinery", Medical Systems for Industry, info@medicalsysforindustry.com; 2021; 1 pg.

International Search Report and Written Opinion for PCT/IB2020/053491, dated May 25, 2020, 9 pgs.

* cited by examiner

EQUIPMENT FOR WINDING MEDICAL TUBING

RELATED APPLICATIONS

The present application is a national phase of PCT Application No. PCT/IB2020/053491, filed on Apr. 14, 2020, which claims the benefit of EP Application No. EP19169329.0, filed Apr. 15, 2019 and EP Application No. EP19179055.9, filed Jun. 7, 2019. The entire contents of these applications are incorporated herein by reference.

TECHNICAL DOMAIN

The present invention discloses an equipment for winding medical tubing employing automated and sequentially-arranged workstations, which can be operated simultaneously.

STATE OF THE ART

Flexible plastic tubing is produced for a variety of sectors, ranging from engineering (automotive, aerospace), agriculture, horticulture and water management, plumbing, hydraulics, oil and gas, as well as the medical and healthcare. The specifications of the tubing, such as dimensions, material and its chemical and physical properties, are adapted to its specific use, whereby a coiled or wound assembly of the tubing generally eases the packaging, transport, use and manipulation of the tubing. To this end, different types of coiling machines, mostly employing motorised rotating reels, have been developed for industrial tubing and are available on the market today.

Yet, for the medical sector large-scale automated winding of medical tubing remains an unmet need, with medical tubing still primarily being wound by hand. Apart from the limitations in processing speed and the increased risk of contamination which come with the manual handling of the tubing, inconsistencies in winding and waste of material due to mis-manipulation of the tubing are more likely to occur when compared to an automated process.

Many medical devices include plastic tubing for fluid or gas transfer, Such medical tubing must comply with international norms and display adequate quality requirements concerning its sterility, performance, ingredients, etc.

In its practical application medical tubing is handled by medically-trained professionals, but also by untrained patients. For both user groups a simple and safe manipulation of the medical tubing without the risk of causing damage or entanglement of the tubing, is adamant. In order to mitigate these risks, it is critical to provide the tubing in a suitably organised state, such as a wound or coiled state.

To this end, several solutions for winding medical tubing have been developed employing desk top equipment, by way of example: http://www.medicalsysforindustry.com/custom%20tube%20coilers.html. However, these solutions are extremely limited in their processing rate and are therefore primarily useful for individual laboratories, but not suited for large-scale industrial operations.

CN108313424 describes an automatic winding and bagging mechanism for a medical catheter. The automatic winding and bagging mechanism comprises a rack, a catheter winding mechanism and a bagging grinding device, and the catheter winding mechanism and the bagging grinding device are sequentially arranged on the rack. The throughput of this mechanism is limited.

US2018008798 discloses a device for holding coils of medical tubing to simplify packaging and handling thus making it easier for patient to manipulate each coil of tubing and reducing the probability of entanglement. This solution is particularly suited to organize medical tubing conveying medical fluid in connection with dialysis machines, as it simplifies the handling of the tubing in a clinical or in a domestic setting. However, this method does not provide a solution for winding large volumes of medical tubing at industrial scale.

CN108313424 relates to an automatic winding and bagging mechanism for a medical catheter. The equipment comprises a rack, a catheter winding mechanism and a bagging grinding device. The catheter winding mechanism comprises a workbench, a catheter clamping assembly, a winding disc, a catheter pressing assembly, a catheter containing box and a pushing device.

DE3523848 discloses a device for winding and cutting, in particular medical tubes, with a rotating body to which a clamp and guide for fixing the tube to be wound are attached. The rotating body is rotated in such a way that the tube can be wound and cut to different lengths with an adjustable winding circumference.

The medical catheter winding device disclosed in CN103523560 provides a solution to ensure tight and firm winding of the catheter. It comprises a tensioning mechanism for enabling the catheter to be kept in a tight state when the catheter is wound.

EP1452474 discloses a method for the automated production of bobinless cable coils, wherein the cable strands can be predetermined in their length and are drawn off a cable reel. Each cable strand is wound to a coil and fixed in this form.

U.S. Pat. No. 6,135,164 describes an apparatus for preparing and positioning U-shaped loops of wires on a conveyor of a harness making machine. The invention employs vertically moveable transfer grippers to transfer the wire loops from the cutting station to the grippers of the conveyor.

The advantage of providing medical tubing organized in a wound state is further emphasized in document US2013/0006226 describing a compact catheter assembly, whereby the wound state of the catheter enhances its safe use, thus preventing hygiene-related medical issues.

None of the approaches provided today provides a satisfactory solution for safe, industrial-scale winding of medical tubing at a high and adjustable processing rate.

BRIEF SUMMARY OF THE INVENTION

One objective of the present invention is to provide an equipment for winding medical tubing which is adapted for industrial-scale manufacturing, thereby increasing efficiency of winding medical tubing.

Another objective is to propose an equipment for winding medical tubing which is capable of operating in a controlled environment, thereby reducing the risk of contamination.

According to one aspect, those objectives are achieved by providing an equipment for winding medical tubing, employing a plurality distinct operational units performing automated tasks and which are capable of operating simultaneously comprising:
  (i) one or more conveying units arranged for conveying medical tubing to one or more bending units;
  (ii) one or more said bending units arranged for bending medical tubing in a U shape;
  (iii) one or more loading units adapted for individually picking and transporting each medical tubing after its bending from the bending unit to the winding unit;

(iv) one or more winding units for winding medical tubing, comprising a winding nest arranged for receiving medical tubing from said loading unit, and a winding module adapted for winding medical tubing after its deposition into said winding nest;

The equipment for winding medical tubing may furthermore comprise:

(i) one or more unloading units adapted for individually picking and transporting each medical tubing after its winding from said winding unit to a packaging unit;

(ii) one or more packaging units for packaging each tubing after its winding, said packaging units capable of receiving the wound medical tubing from said unloading unit and employing a sliding cover plate for maintaining medical tubing in its wound state.

According to another aspect, said one or more operational units can be arranged and combined with other operational units in sequentially arranged and simultaneously operating working stations, including (i) one or more preparation stations each comprising said conveying unit(s)s said bending unit(s); and/or (ii) one or more winding stations for winding medical tubing, each comprising said winding units) arranged on a winding station plate;

This equipment effectively solves the above-mentioned problems of the prior art with automated, sequentially-arranged units and sequentially arranged workstations which can operate simultaneously and are adapted for industrial-scale manufacturing to match a specific production line speed, thereby increasing efficiency and safety of winding and packaging medical tubing.

Each workstation can comprise a plurality of units in parallel and/or serial arrangement.

The number of units of each type might be increased to improve the through put.

The number of workstations of each type might be increased to improve the throughput.

The number of units and/or workstations of different types might be different. For example, the number of slow units with a low throughput might be higher that the number of fast units with a higher throughput.

Different units and/or units of the same type might be mounted in parallel. For example, the equipment might comprise a plurality of bending units in parallel, and/or a plurality of winding units and/or winding stations in parallel.

Workstation of the same type may be mounted in parallel arrangement. Workstation of different types may be mounted in serial arrangement.

Optionally, the equipment may further comprise one or more said packaging units for packaging each tubing after its winding, said packaging units.

The arrangement of the units permits the equipment to operate efficiently and at a high and adjustable throughput rate due to the following favourable aspects:

(i) The process is fully automated, and
(ii) a plurality of each workstation as well as a plurality of each unit can be employed, and
(iii) the units of the workstations are capable of operating simultaneously
(iv) the processing speed of each unit and the number of each unit and workstation can be optimised to achieve a favourable throughput rate.

Advantageously, in the bending unit the medical tubing is arranged in a "U"-shape with optimal dimensions for the winding process in the winding unit.

As a further advantage, the ratio between the number of bending units, the number of loading units and the number of winding stations can be optimised to achieve efficient and smooth operations as well as a favourable throughput rate.

Furthermore, this advantageous "U"-shape is maintained by the loading unit throughout the transfer of the medical tubing to the winding unit. The disposition of the medical tubing in said "U" shape which is adjusted to the dimension of the winding unit permits consistent and rapid winding without straining or damaging the medical tubing.

Advantageously, the distal end of the tubing is received below the plate of the winding station by rotatable jaws, which are connected to and rotating with the winding module, permitting winding of the medical tubing around the vertical axis of the winding module, thus facilitating a favourable compact arrangement of several winding units.

As an additional advantage, the rotatable jaws are operated by fixed jaw grippers which are actuated by an independent motor, thus permitting the rotatable jaws an unlimited range of freedom.

The rotatable jaws favourable perform a rotating movement along the vertical axis of the winding module together with the rotating winding core, which is actuated by a motor.

For the duration of the automated winding of the medical tubing around the axis, tube jaws favourably keep the tube positioned within the winding nest and below the level of the winding station plate.

The wound medical tubing is advantageously raised along the vertical axis to the level of the winding station plate in a controlled movement preventing the tubing from being compressed or damaged and presented to the grippers of the unloading unit which optionally transfer the medical tubing to the packaging unit.

Advantageously, the ratio between the number of winding stations, which may contain a plurality of winding units, and the number of the unloading units can be optimised to achieve efficient and coordinated operations as well as a favourable throughput rate.

Once the medical tubing has been placed in the packaging container a cover plate is advantageously positioned over it in an automated gliding movement, which prevents the unwinding of the wound medical tubing.

BRIEF DESCRIPTION OF THE FIGURES

Examples of the practical implementation of the invention are disclosed in the description and illustrated by the attached figures of which.

DETAILED DESCRIPTION OF THE INVENTION

Figure 1:
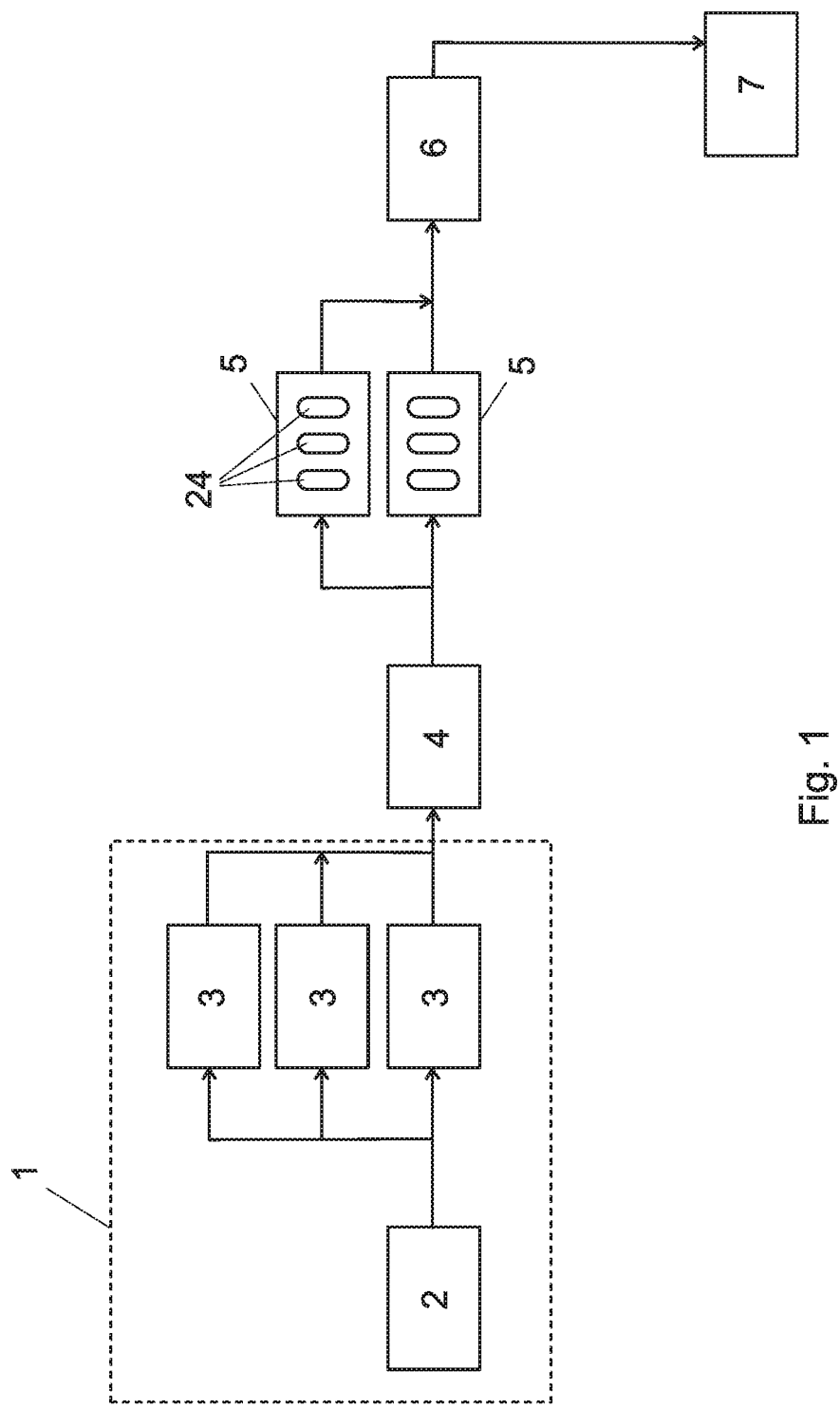
FIG. 1 is a schematic representation of the modular organisation of the operational units and workstations.

The present invention describes an equipment for automated winding of medical tubing employing sequentially arranged operational units and workstations, comprising a plurality of units. A first workstation 1, called preparation station, comprises at least one conveying unit 2 and at least one bending unit 3. A second workstation 5, called winding station, comprises at least one, but preferably a plurality of winding units 24. One or more loading units 4 connect the operational processes of the preparation station 1 to the winding station 5. One or more unloading units 6 connect the operational processes of the winding station 5 to a packaging unit 7.

The equipment of the present invention is configured to wind different type of medical tubing 10, such as but not limited to catheters, dialysis tubing, fluid management (drainage), respiratory equipment, biopharmaceutical equipment and others.

Figure 4:
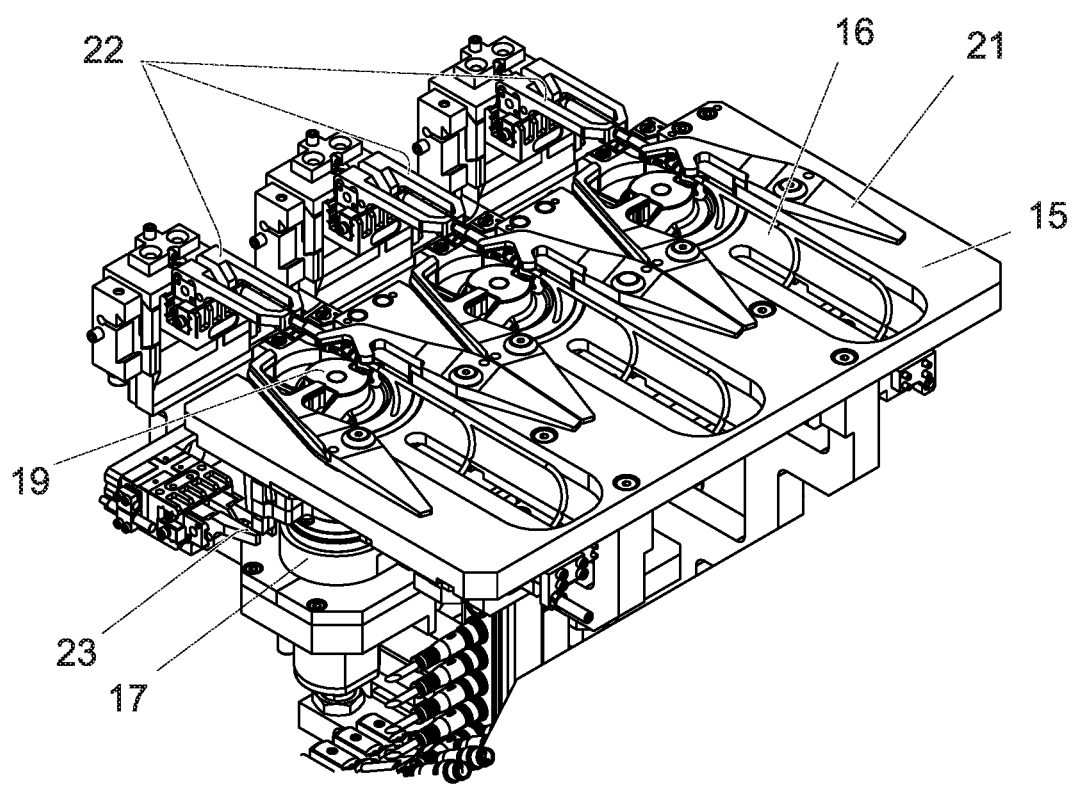
FIG. 4 is a schematic representation of the winding station.

FIG. 1 exemplifies an arrangement of the equipment comprising a preparation station 1, a loading unit 4, two winding stations 5, an unloading unit 6 and a packaging unit 7. The preparation station 1 comprises a conveying unit 2 configured to dispose medical tubing 10 (FIG. 2) into three bending units 3. The medical tubing 10 (FIG. 2) might be transferred by the loading unit 4 servicing two separate winding stations 5 comprising each three of winding units 24, each comprising a winding nest 16 (FIG. 4) and three winding modules 17 (FIG. 4). The unloading unit 6 might be configured to alternatingly remove medical tubing 10 (FIG. 2) from two winding stations 5 and transfer it to the packaging unit 7, The above-mentioned numbers of workstations and different units are intended to be an example and can be varied according to specific needs.

Optionally, the loading unit 4 and the unloading unit 6 might be equipped with sensors able to detect, if a receiving cavity, such as the winding nest 16 (FIG. 4) or the packaging container, is unloaded before the deposition of the medical tubing 10 (FIG. 4) in either the receiving cavity, thus enabling the equipment to operate in a highly coordinated and efficient manner.

Optionally, the winding station 5 might be moved from proximity of the preparation station 1 to proximity of the packaging unit 7 during the winding process in order to minimise the transfer distances of the medical tubing 10 and to increase efficiency of the process.

Figure 2A:
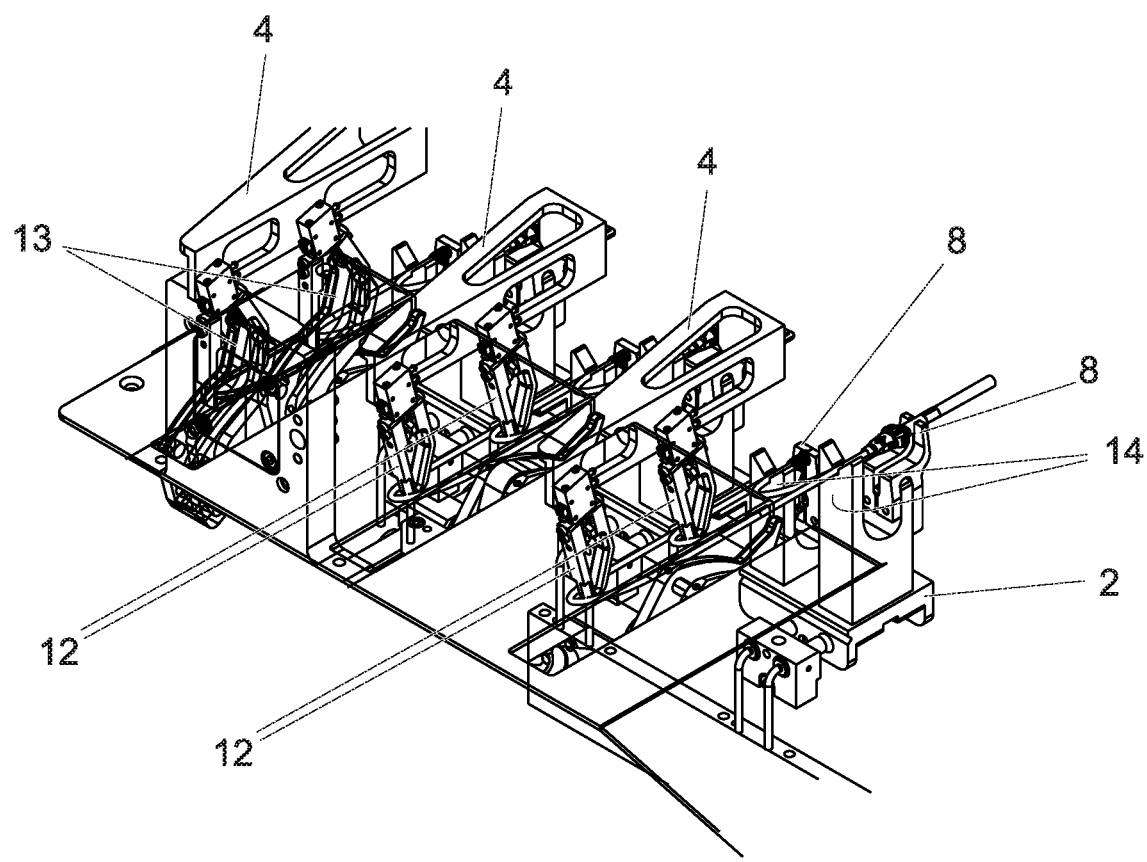
FIG. 2A is a schematic representation of the preparation station.
Figure 2B:
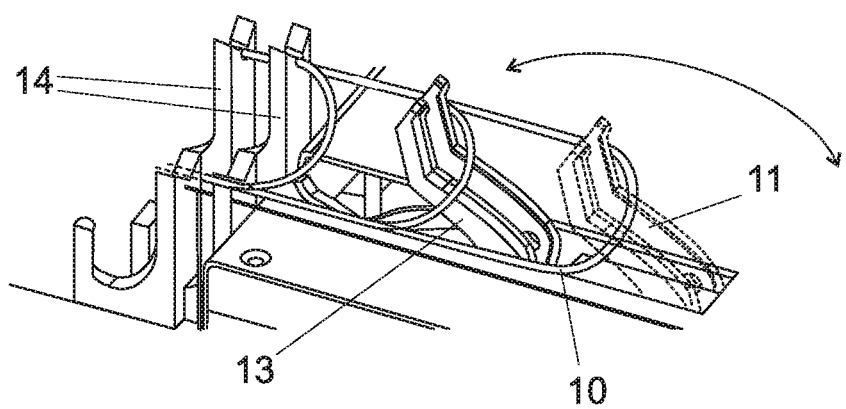
FIG. 2B is a perspective view of the bending unit lever indicating the direction of its automated movement.

FIG. 2A illustrates the possible composition of a preparation station comprising a conveying unit 2 and three sequentially arranged bending units 3 and parts of the loading unit 4 with its tube grippers 12. FIG. 2B illustrates the binding unit lever 13 in two possible positions, wherein its rotating movement performed to stretch the bent medical tubing 10 is indicated by arrows.

As shown in FIGS. 2A and 2B, the ends of the medical tubing 10 are fastened by end grippers 8 of the bending unit 3 and arranged in a "U" shape with the aid of two open end grippers 14 located next to the end grippers 8 and a lever 13, which moves the middle section of the medical tubing 10 in the opposite direction of its ends. The distance between the end grippers 8 configured to fasten the medical tubing 10 and the lever 13 can be adapted to suit the length of the medical tubing.

Figure 3:
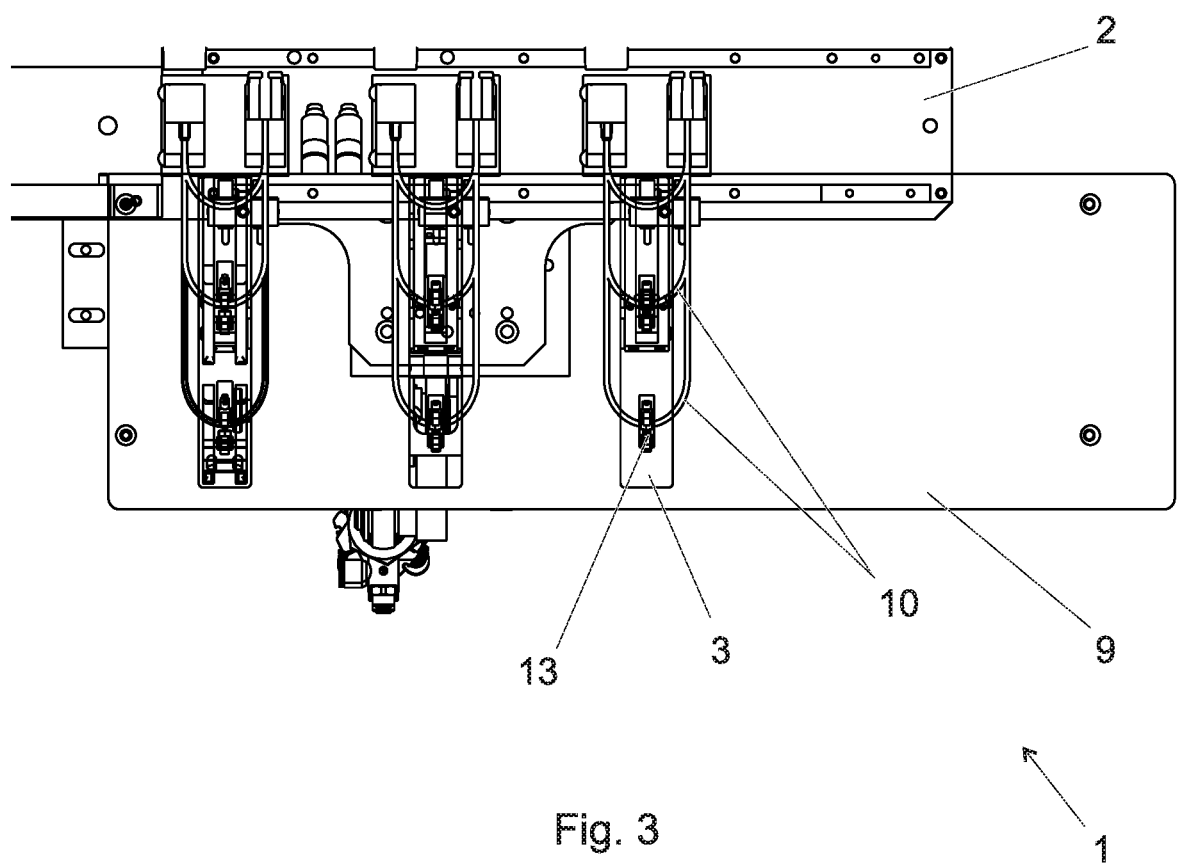
FIG. 3 is a top view of the preparation station, identifying the conveying unit and the bending unit.

FIG. 3 illustrates the preparation station 1, in which the medical tubing 10 is delivered to the binding unit 3 by the conveying unit 2, which employs end grippers 8 (FIG. 2A) to fasten the ends of the medical tubing 10.

The medical tubing 10 is received in its "U" shape by the loading unit 4 (FIG. 1), which comprises a plurality of grippers to transfer and subsequently dispose the medical tubing 10 in its maintained "U" shape in the winding nest 16 of the winding station 5, which is depicted in FIG. 4. For each piece of medical tubing 10, the loading unit 4 (FIG. 2A) employs two end grippers grasping the ends of the medical tubing and one tube gripper 12 (FIG. 2A) grasping the middle section of the medical tubing. The plurality of grippers is adjusted to suit the plurality of bending units 3 and the plurality of winding stations 5. The loading unit 4 (FIG. 1) can transfer medical tubing 10 to a plurality of winding stations 5 (FIG. 1) in an alternating manner.

Figure 5:
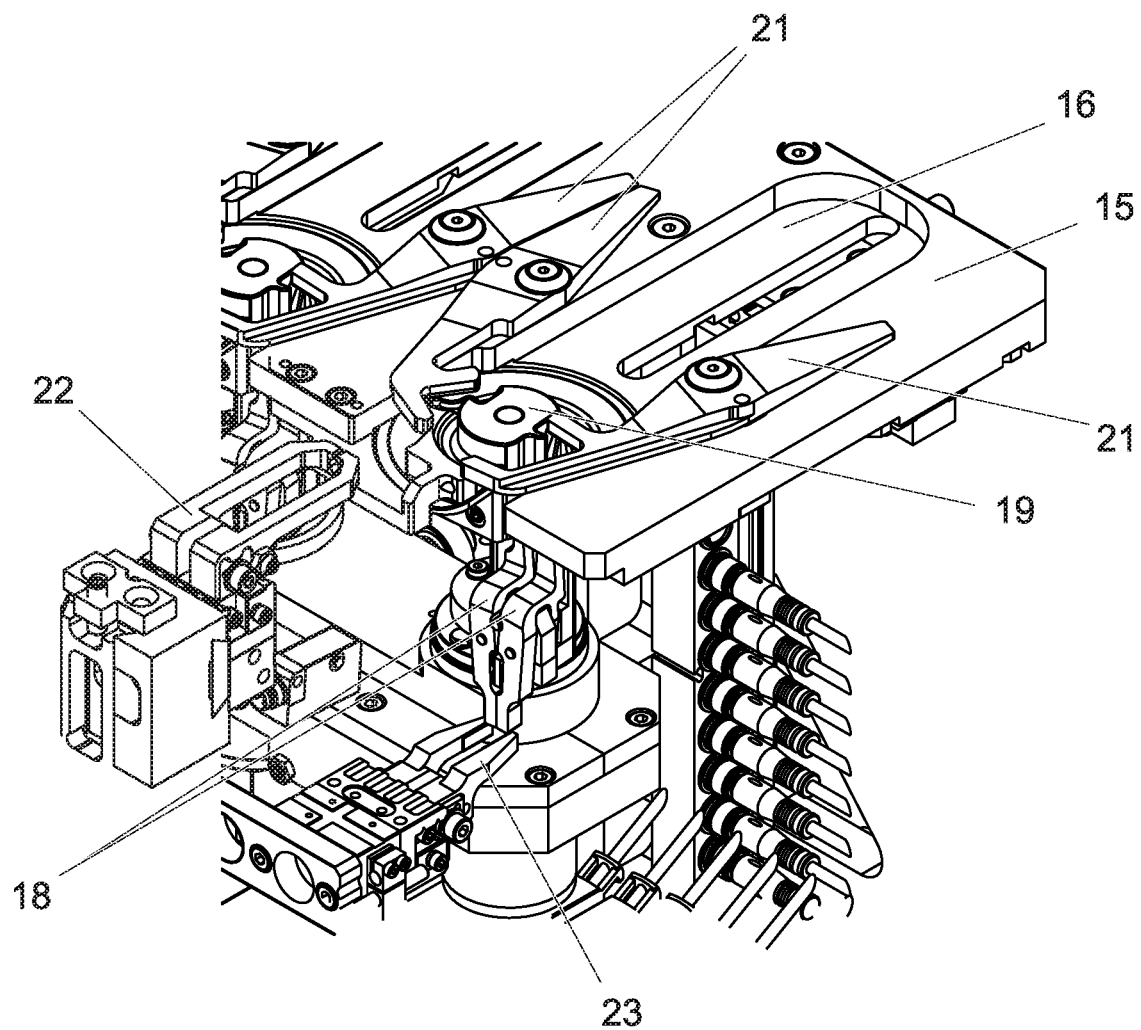
FIG. 5 is a perspective view of a winding unit from above the winding station plate, comprising the winding nest and the winding module.
Figure 6:
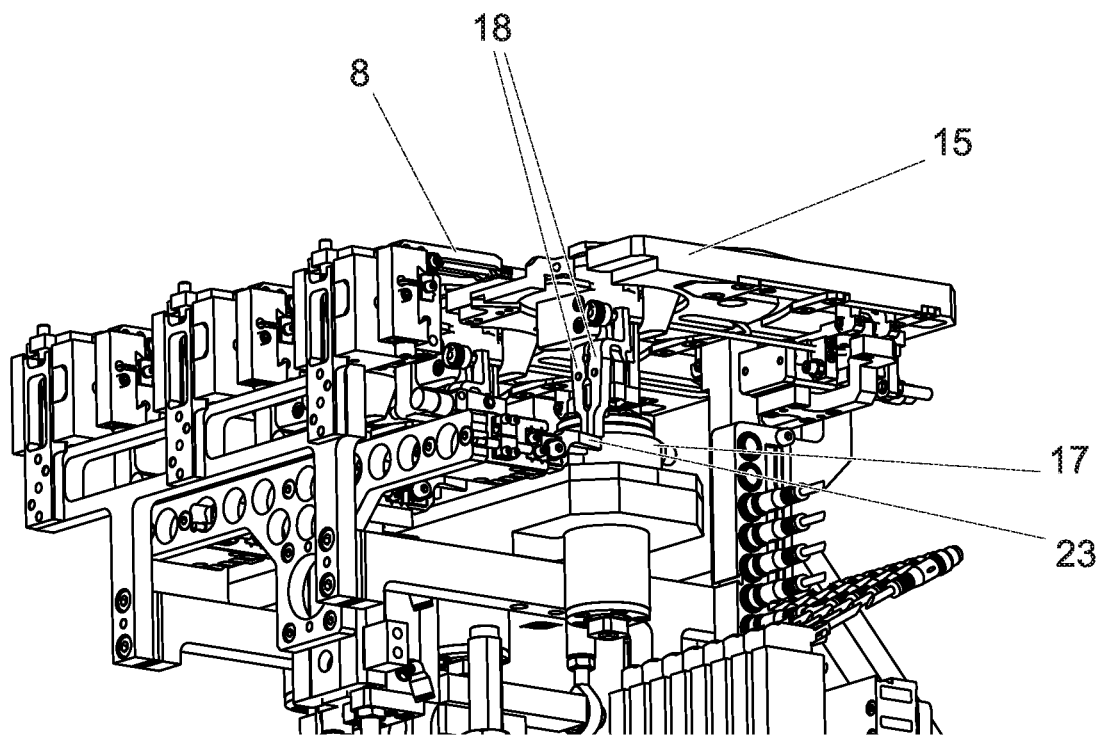
FIG. 6 is a perspective view of the winding unit from below the winding station plate.
Figure 7A:
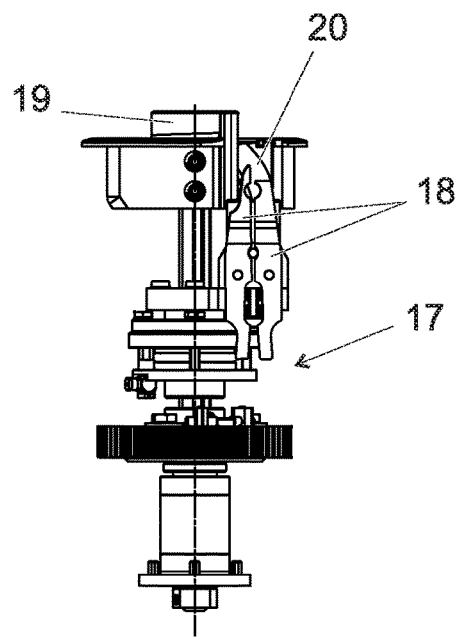
FIG. 7A is a side view of the winding module
Figure 7B:
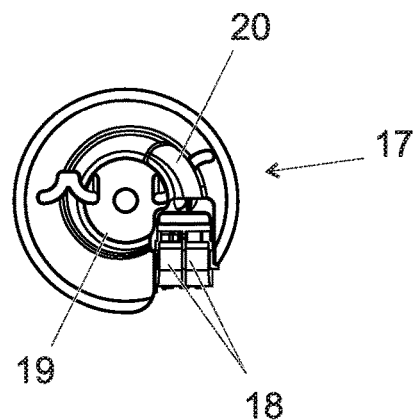
FIG. 7B is a top view of the winding module
Figure 7C:
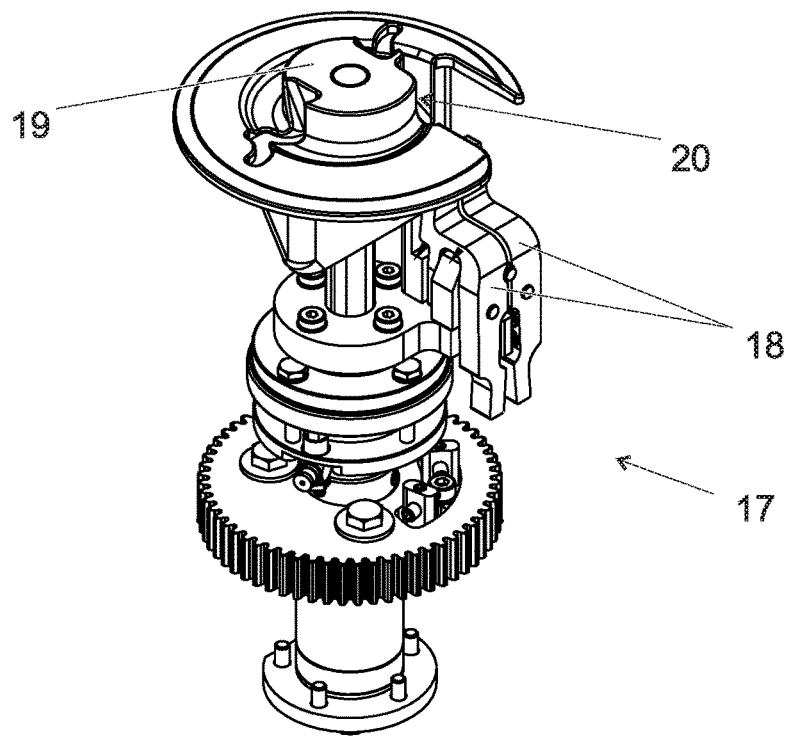
FIG. 7C is a perspective view of the winding module

The medical tubing 10 is configured to be positioned in the winding nest 16, shown in FIG. 4, which is milled into a winding station plate 15, whereby the distal end of the medical tubing is lowered into a descending groove 20 as shown in in FIGS. 7 A to C. The ends of the medical tubing are fastened by a fixed gripper 22 at the level of the winding station plate 15 and by rotatable jaws 18 (FIG. 5), which are actuated by fixed jaw grippers 23 (FIG. 5) and positioned below the winding station plate 15.

In a subsequent step, the medical tubing 10 is wound vertically around the winding core 19 of the winding module as shown in FIGS. 7 A to C, whereby the rotatable jaws 18 clasping one end of the medical tubing are attached to and perform the rotating movement with the winding module 17.

The winding of the medical tubing 10 around the vertical axis of the winding core 19, as opposed to horizontal coiling in a disc-like shape, facilitates a compact arrangement with several winding units 24 in parallel, as shown in FIG. 4.

During the automated winding of the medical tubing around the winding core 19, tube jaws 2:1 (FIG. 5), which are connected to the winding station plate 15 and can be moved into close proximity of the winding core 19 and away from it in a rotating movement, keeping the medical tubing positioned within the winding nest 16 and below the level of the winding station plate 15.

The wound medical tubing is raised to the level of the winding station plate 15 (FIG. 5) and received by the unloading unit 6 (FIG. 1), which employs a plurality of grippers suited to the number of medical tubing to be transferred. The unloading unit 6 subsequently transfers the medical tubing to the packaging unit 7 (FIG. 1).

Upon release and deposition of the medical tubing in the packaging container, a sliding cover plate is moved onto the packaging container in a gliding movement in order to prevent the wound medical tubing from unwinding.

REFERENCE NUMBERS USED IN THE FIGURES

1 Preparation station
2 Conveying unit
3 Bending unit
4 Loading unit
5 Winding station
6 Unloading unit
7 Packaging unit
8 End grippers
9 Bending station plate
10 Medical tubing
11 Alternative lever position adjusted to length of tubing
12 Tube gripper
13 Lever
14 Open end grippers
15 Winding station plate
16 Winding nest
17 Winding module
18 Rotatable jaws
19 Winding core
20 Descending groove 21 Tube jaws
22 Fixed grippers
23 Fixed jaw grippers
24 Winding unit

The invention claimed is:

1. An equipment for winding medical tubing, the equipment comprising:
   (i) one or more conveying units arranged for conveying medical tubing to one or more bending units;
   (ii) said one or more bending units arranged for bending medical tubing in a U-shape;
   (iii) one or more loading units adapted for individually picking and transporting each medical tubing after its bending; and
   (iv) one or more winding units—for winding medical tubing, the one or more winding units comprising a winding nest arranged for receiving medical tubing from said one or more loading units, and a winding module adapted for winding medical tubing after its deposition into said winding nest.

2. The equipment of claim 1, further comprising:
   (i) one or more unloading units adapted for individually picking and transporting each medical tubing after its winding;
   (ii) one or more packaging units for packaging each tubing after its winding, said one or more packaging units employing a sliding cover plate for maintaining medical tubing in its wound state.

3. The equipment according to claim 2, wherein the one or more unloading units are equipped with grippers capable of grasping, transferring, and releasing the wound medical tubing.

4. The equipment according to claim 2, said one or more packaging units being equipped with packaging containers capable of receiving the wound medical tubing from said one or more unloading units, said sliding cover plate being capable of being placed onto one of the packaging containers in a gliding movement.

5. The equipment according to claim 4, comprising a plurality of sliding cover plates.

6. The equipment of claim 2, wherein one or more distinct operational units are organized into automated, sequentially arranged workstations capable of operating simultaneously.

7. The equipment of claim 1, comprising a plurality of said bending units in parallel.

8. The equipment of claim 1, comprising a plurality of said winding units in parallel.

9. The equipment of claim 1, wherein one or more distinct operational units are organized into automated, sequentially arranged workstations capable of operating simultaneously, the workstations including:
   (i) one or more preparation stations comprising said one or more conveying unit(s) and said one or more bending unit; and
   (ii) one or more winding stations comprising said one or more winding unit(s).

10. The equipment of claim 1, said one or more conveying units comprising end grippers arranged for fastening proximal and distal ends of the medical tubing and open end grippers for positioning the medical tubing, and said one or more bending units comprising a lever arranged for pulling a middle section of the medical tubing in a direction opposite the end grippers, so as to arrange the medical tubing in the U shape.

11. The equipment of claim 1, said one or more loading units comprising for each piece of medical tubing two end grippers capable of grasping ends of the medical tubing and one tube gripper capable of grasping a middle section of the medical tubing and transferring the piece of medical tubing to said one or more winding units.

12. The equipment according to claim 1, wherein each of said one or more winding units comprises:
   (i) said winding nest, which is cut into a winding station plate, said winding nest comprising a descending groove and being adapted for receiving the U-shaped medical tubing from the one or more loading units;
   (ii) two tube jaws capable of keeping the medical tubing positioned within said winding nest and below a surface of said plate-, a descending groove adapted for presenting a distal end of the medical tubing to rotatable jaws;
   (iii) a rotatable winding core powered by a fixed motor;
   (iv) a fixed gripper-capable of fastening a proximal end of the medical tubing; and
   (v) a fixed jaw gripper capable of actuating said rotatable jaws.

13. The equipment according to claim 12, further comprising a fixed motor for actuating said fixed jaw gripper, wherein the rotatable jaws and the fixed jaw gripper are located below said winding station plate.

14. A method employing an equipment according to claim 1, to wind medical tubing in an automated process, the method comprising the steps of:
   i) conveying the medical tubing with said one or more conveying units;
   ii) arranging the medical tubing in a U shape in said one or more bending units;
   iii) individually picking each tubing and placing it onto said one or more winding units;
   iv) receiving said tubing from said one or more loading units in said winding nest of said one or more winding units; and
   v) winding the medical tubing after its deposition into said winding nest.

15. The method according to claim 14, wherein the medical tubing is moved into position in said winding nest by said one or more loading units, wherein a proximal end of the medical tubing is fastened by a fixed gripper at a level of a winding station plate and wherein a distal end of the medical tubing is lowered into a descending groove of said winding station and fastened by rotatable jaws which are actuated by a motorized fixed jaw gripper located below said winding station plate and which perform a rotating movement together with a winding core which is actuated by a motor.

* * * * *